(12) United States Patent
Taketomi et al.

(10) Patent No.: US 12,322,264 B2
(45) Date of Patent: Jun. 3, 2025

(54) DATA PROCESSOR, CARE SUPPORT SYSTEM, AND DATA PROCESSING METHOD

(71) Applicant: PARAMOUNT BED CO., LTD., Tokyo (JP)

(72) Inventors: Takumi Taketomi, Tokyo (JP); Masato Shimokawa, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 152 days.

(21) Appl. No.: 18/106,907

(22) Filed: Feb. 7, 2023

(65) Prior Publication Data

US 2024/0021063 A1 Jan. 18, 2024

(30) Foreign Application Priority Data

Jul. 14, 2022 (JP) .................. 2022-113256

(51) Int. Cl.
*G08B 21/04* (2006.01)
*A61B 5/00* (2006.01)

(52) U.S. Cl.
CPC ........ *G08B 21/0461* (2013.01); *A61B 5/4205* (2013.01); *G08B 21/043* (2013.01); *G08B 21/0476* (2013.01)

(58) Field of Classification Search
CPC .............. G08B 21/0461; G08B 21/043; G08B 21/0476; A61B 5/4205
See application file for complete search history.

(56) References Cited

U.S. PATENT DOCUMENTS

| | | | | |
|---|---|---|---|---|
| 6,616,607 B2 * | 9/2003 | Hashimoto | ........... | A61B 5/1113 128/903 |
| 7,499,741 B2 * | 3/2009 | Diab | .................... | A61B 5/7257 600/336 |
| 8,665,333 B1 * | 3/2014 | Sharma | ............ | G08B 13/19643 348/169 |
| 11,227,187 B1 * | 1/2022 | Weinberger | ............. | G10L 15/19 |
| 12,161,461 B2 * | 12/2024 | Sivertsen | ............... | A61B 5/747 |

(Continued)

FOREIGN PATENT DOCUMENTS

| | | | | |
|---|---|---|---|---|
| EP | 3346402 A1 * | 7/2018 | .......... | A61B 5/1117 |
| EP | 4336210 A1 * | 3/2024 | .......... | G01S 13/003 |

(Continued)

*Primary Examiner* — Chico A Foxx
(74) *Attorney, Agent, or Firm* — Birch, Stewart, Kolasch & Birch, LLP

(57) ABSTRACT

According to an embodiment, a data processor includes an acquisitor to acquire a first data; and a processor to conduct a first operation. At least a part of the first data is obtained from a first sensor to detect a state of a human subject. The processor outputs, if the first data includes a first data information, a first event prediction information related to an occurrence of a first event related to the human subject, and a state prediction information related to a state to be predicted of the human subject at the occurrence of the first event, in the first operation. The occurrence of the first event is detected by a second sensor to detect the state of the human subject. The state to be predicted of the human subject at the occurrence of the first event is not detected by the second sensor.

23 Claims, 8 Drawing Sheets

(56) References Cited

U.S. PATENT DOCUMENTS

| | | | |
|---|---|---|---|
| 2003/0236474 A1* | 12/2003 | Singh | A61B 5/4094 600/595 |
| 2005/0151640 A1* | 7/2005 | Hastings | G16H 40/67 340/539.11 |
| 2006/0053342 A1* | 3/2006 | Bazakos | G08B 13/19682 714/37 |
| 2007/0250901 A1* | 10/2007 | McIntire | H04N 21/47815 348/E7.071 |
| 2010/0034462 A1* | 2/2010 | Nevatia | G06V 10/50 382/190 |
| 2011/0102181 A1* | 5/2011 | Metz | A61B 5/1115 340/575 |
| 2011/0112442 A1* | 5/2011 | Meger | A61B 5/7203 600/595 |
| 2014/0157031 A1* | 6/2014 | Aoyagi | G06F 1/325 713/323 |
| 2014/0168397 A1* | 6/2014 | Greco | G16Z 99/00 348/77 |
| 2014/0333775 A1* | 11/2014 | Naikal | H04N 21/44008 348/159 |
| 2015/0199892 A1* | 7/2015 | Johnson | G08B 31/00 348/77 |
| 2016/0125759 A1* | 5/2016 | Dougherty | G09B 19/0076 434/236 |
| 2016/0292988 A1* | 10/2016 | McCleary | G08B 21/0446 |
| 2017/0065464 A1* | 3/2017 | Heil | A61B 5/202 |
| 2017/0150905 A1* | 6/2017 | Shen | G08B 21/0453 |
| 2018/0122207 A1* | 5/2018 | Noda | A61B 5/743 |
| 2018/0228404 A1* | 8/2018 | Bhunia | A61B 5/6817 |
| 2018/0233018 A1* | 8/2018 | Burwinkel | A61B 5/1117 |
| 2019/0139390 A1* | 5/2019 | Kawazu | G08B 21/043 |
| 2019/0164403 A1* | 5/2019 | Ishikawa | G08B 21/0469 |
| 2019/0228866 A1* | 7/2019 | Weffers-Albu | G16H 40/63 |
| 2020/0015762 A1* | 1/2020 | Mayoras, Jr. | A61B 5/0022 |
| 2020/0205746 A1* | 7/2020 | Burwinkel | G08B 21/0446 |
| 2021/0158965 A1* | 5/2021 | Receveur | G16H 50/20 |
| 2021/0241912 A1* | 8/2021 | Chazin | G08B 21/0446 |
| 2021/0401380 A1* | 12/2021 | Meyerson | A61B 5/6892 |
| 2022/0054078 A1* | 2/2022 | Kanemaru | A61B 5/6822 |
| 2022/0111528 A1* | 4/2022 | Dhamasia | B25J 19/06 |
| 2022/0366244 A1* | 11/2022 | Vandeventer | G05B 17/00 |
| 2023/0004795 A1* | 1/2023 | Peric | G06F 18/2178 |
| 2023/0120653 A1* | 4/2023 | Zerhusen | A61G 7/015 700/279 |
| 2023/0144166 A1* | 5/2023 | Alford | G06N 20/00 706/12 |
| 2023/0177391 A1* | 6/2023 | Packwood | G06V 20/52 706/12 |
| 2023/0375693 A1* | 11/2023 | El-Akkad | G01S 13/60 |
| 2023/0408619 A1* | 12/2023 | El-Akkad | G01S 5/0278 |
| 2024/0105299 A1* | 3/2024 | Keene | G06F 3/011 |
| 2024/0194035 A1* | 6/2024 | Bergmann | G06Q 20/208 |
| 2024/0358331 A1* | 10/2024 | Au | A61B 5/6823 |

FOREIGN PATENT DOCUMENTS

| | | | | |
|---|---|---|---|---|
| JP | 2015021754 A | * | 2/2015 | |
| JP | 2021-18760 A | | 2/2021 | |
| KR | 2021096384 A | * | 8/2021 | |
| WO | WO-2022159214 A2 | * | 7/2022 | G06T 7/0004 |

* cited by examiner

DATA PROCESSOR, CARE SUPPORT SYSTEM, AND DATA PROCESSING METHOD

CROSS-REFERENCE TO RELATED APPLICATIONS

This application is based upon and claims the benefit of priority from Japanese Patent Application No. 2022-113256, filed on Jul. 14, 2022; the entire contents of which are incorporated herein by reference.

FIELD

Embodiments of described herein generally relate to a data processor, a care support system, and a data processing method.

BACKGROUND

In care, data to be obtained from various kinds of sensors is used. The data is appropriately processed to enable suitable care to be conducted.

DETAILED DESCRIPTION

Figure 1:
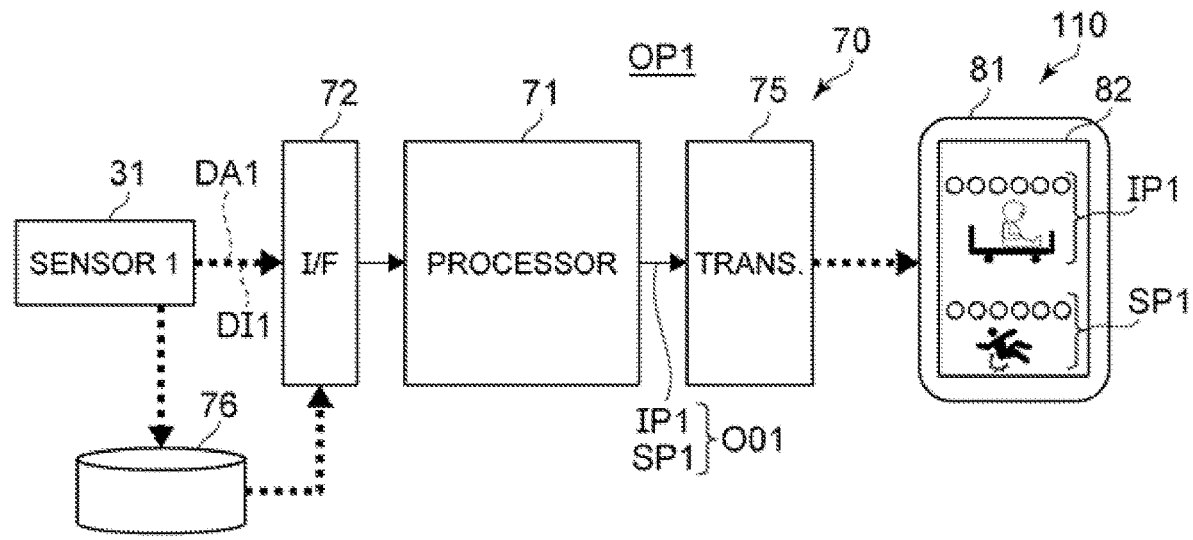
FIG. 1 is an exemplary schematic diagram illustrating a data processor according to a first embodiment.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to or cover a computer-related entity or an entity related to an operational apparatus with one or more specific functionalities, wherein the entity can be either hardware, or a combination of hardware and software in execution.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can include a processor therein to execute software stored on a non-transitory electronic memory or firmware that confers at least in part the functionality of the electronic components. While various components have been illustrated as separate components, it will be appreciated that multiple components can be implemented as a single component, or a single component can be implemented as multiple components, without departing from example embodiments. Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer-readable (or machine-readable) device or computer-readable (or machine-readable) storage/communications media having a computer program stored thereon. For example, computer readable storage media can include, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, including, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

In general, one aspect of the present application is a data processor including:
- an acquisitor configured to acquire a first data; and
- a processor configured to conduct a first operation based on the first data acquired by the acquisitor,
- at least a part of the first data being obtained from a first sensor configured to detect a state of a human subject,
- the processor being configured to output, if the first data includes a first data information, a first event prediction information related to an occurrence of a first event related to the human subject, and a state prediction information related to a state to be predicted of the human subject at the occurrence of the first event, in the first operation,
- the occurrence of the first event being configured to be detected by a second sensor configured to detect the state of the human subject, and
- the state to be predicted of the human subject at the occurrence of the first event being configured not to be detected by the second sensor.

Hereinafter, embodiments of the invention will be described with reference to the drawings.

In the specification of the present application and the respective drawings, the similar elements having been described related to the already described drawing are assigned with the same reference numerals, and detailed descriptions thereof are omitted as appropriate.

First Embodiment

FIG. 1 is an exemplary schematic diagram illustrating a data processor according to a first embodiment.

As illustrated in FIG. 1, a data processor 70 according to the embodiment includes an acquisitor 72 and a processor 71. A care support system 110 according to the embodiment includes the data processor 70

The acquisitor 72 is configured to acquire first data DA1. The acquisitor 72 is, for example, an interface. The processor 71 is configured to conduct a first operation OP1 based on the first data DA1 acquired by the acquisitor 72.

At least a part of the first data DA1 is obtained from a first sensor 31. The first sensor 31 is configured to detect a state of a human subject. For example, the human subject is a care receiver. A user of the care support system 110 is a care giver. The care giver provides care to the care receiver.

In the embodiment, data obtained from the first sensor 31 may be supplied to a memory 76, and may be stored in the memory 76. The first data DA1 stored in the memory 76 may be supplied to the acquisitor 72. The memory 76 may be provided to a server or the like. The server may be provided at an arbitrary place. The acquisitor 72 may acquire the first data DA1 by an arbitrary wireless or wired method.

The processor 71 is configured to output state prediction information SP1 when the first data DA1 includes specific first data information DI1, in the first operation OP1. The processor 71 may be configured to output first event prediction information IP1 when the first data DA1 includes the specific first data information DI1, in the first operation OP1. The processor 71 is configured to output an output information OO1 including the first event prediction information IP1 and the state prediction information SP1, for example, when the first data DA1 includes specific data, in the first operation OP1.

The first event prediction information IP1 relates to, for example, an occurrence of a first event related to the human subject. The state prediction information SP1 relates to, for example, at the occurrence of the first event related to the human subject, a state to be predicted of the human subject.

In one example, the first event includes at least either of bed-leaving by the human subject and excretion by the human subject. In this case, the state to be predicted of the human subject at the occurrence of the first event includes, for example, a prediction of at least either of a fall and a tumble. The fall includes, for example, falling from a standing posture or a seated posture into a lower position (for example, a floor). The tumble includes, for example, abrupt movement of the body from a bed, a chair, or the like to the floor. The state to be predicted may include an abnormal state of the human subject at the occurrence of the first event.

In the embodiment, a sensor (second sensor) different from the first sensor 31 is configured to detect the occurrence of the first event (for example, bed-leaving or excretion). The second sensor is configured to detect a state of the human subject. The second sensor is, for example, a bed-leaving sensor that detects bed-leaving or an excretion sensor that detects excretion.

Meanwhile, the abovementioned second sensor does not detect a state to be predicted of the human subject at the occurrence of the first event. For example, when the second sensor is the bed-leaving sensor or the excretion sensor, the second sensor does not detect a state to be predicted (a high possibility or the like of the fall, the tumble, or the like).

In the first operation OP1 in the embodiment, the processor 71 outputs the first event prediction information IP1 related to the prediction of the occurrence of the first event that is detectable by the second sensor. In addition, the processor 71 outputs additional information that is not detected by the second sensor, as the state prediction information SP1. For example, in addition to the prediction (the first event prediction information IP1) of the occurrence of bed-leaving, excretion, or the like, the prediction (the state prediction information SP1) that a possibility of the fall or the tumble in the first event is higher than usual is output.

The user (care giver) of the data processor 70 according to the embodiment can know not only the prediction of the occurrence of the first event related to the human subject (for example, the care receiver), but also the prediction of an abnormal state in which a possibility of the occurrence in that time is high. With the embodiment, the data processor that allows more suitable processing can be provided.

As illustrated in FIG. 1, for example, the output information OO1 (the first event prediction information IP1 and the state prediction information SP1) from the processor 71 is supplied to a communicator 75. The communicator 75 is configured to provide the output information OO1 to an external device. The external device is, for example, a terminal device 81 that is used by the user. The terminal device 81 is, for example, a communication terminal, a computer, or the like. The terminal device 81 may include, for example, portable electronic equipment (for example, a smartphone). For example, the terminal device 81 includes an output part 82. The output part 82 includes, for example, a display. For example, the output information O01 (the first event prediction information IP1 and the state prediction information SP1) is displayed on the output part 82. The output part 82 is configured to output the first event prediction information IP1 and the state prediction.

For example, the first event prediction information IP1 and the state prediction information SP1 are displayed on the output part 82. The first event prediction information IP1 may include, for example, at least any of character information, image information, and a pictogram. The state prediction information SP1 may include, for example, at least any of character information, image information, and a pictogram.

For example, when the first event is bed-leaving, the output part 82 is configured to display character information (text information) related to the prediction of the bed-leaving, as the first event prediction information IP1. The output part 82 is configured to display character information (text information) related to time or the like at which the bed-leaving is predicted to occur, as the first event prediction information IP1. The output part 82 is configured to display image information or a pictogram indicating that the bed-leaving is predicted, as the first event prediction information IP1.

For example, when the first event is bed-leaving, the output part 82 is configured to display character information (text information) on the prediction of an abnormal state (for example, a possibility of the fall, the tumble, or the like is high), as the state prediction information SP1. The output part 82 is configured to display image information or a pictogram indicating that an abnormal state is predicted, as the state prediction information SP1.

The user can acquire, due to an output (for example, displaying) by the output part 82, a prediction (possibility) of the occurrence of the first event of the human subject, and a prediction (possibility) related to a state (abnormal state or the like) in the first event. The user can know the possibility of the occurrence of the first event before the occurrence of the first event. For example, the user knows in advance the possibility of the abnormal state, so that the user can supply more suitable care to the care receiver.

The care support system 110 according to the embodiment may include the data processor 70 and the first sensor 31. The care support system 110 may further include the terminal device 81. With the care support system 110 according to the embodiment, more suitable care can be supplied to the care receiver. A plurality of the terminal devices 81 may be provided with respect to the single data processor 70.

The output part 82 that is provided to the terminal device 81 may output the first event prediction information IP1 and the state prediction information SP1 by sound. The output part 82 may include a speaker. The output part 82 may output the first event prediction information IP1 and the state prediction information SP1 by vibration or the like.

In the embodiment, the state prediction information SP1 includes, for example, a prediction that the human subject performs the first event in a hurry. For example, as mentioned above, when the first data DA1 includes the first data information DI1, the processor 71 is configured to predict an occurrence of the first event (for example, bed-leaving). At this time, the processor 71 is configured to predict a high possibility that the human subject performs the first event (for example, bed-leaving) in a hurry, based on the first data information DI1. When the human subject performs the first event in a hurry, a possibility of a fall or a tumble is high. The state prediction information SP1 includes, for example, a prediction of an abnormal state.

The abnormal state includes, for example, as mentioned above, performing the first event in a hurry than usual. The abnormal state includes, for example, a fall, a tumble, or the like. The abnormal state may include at least any of incontinence, aspiration, insomnia, wandering, an abnormal body condition, and the like. An example of the derivation of the state prediction information SP1 will be described later.

Hereinafter, an example of sensors that are used in the embodiment will be described.

Figure 2:
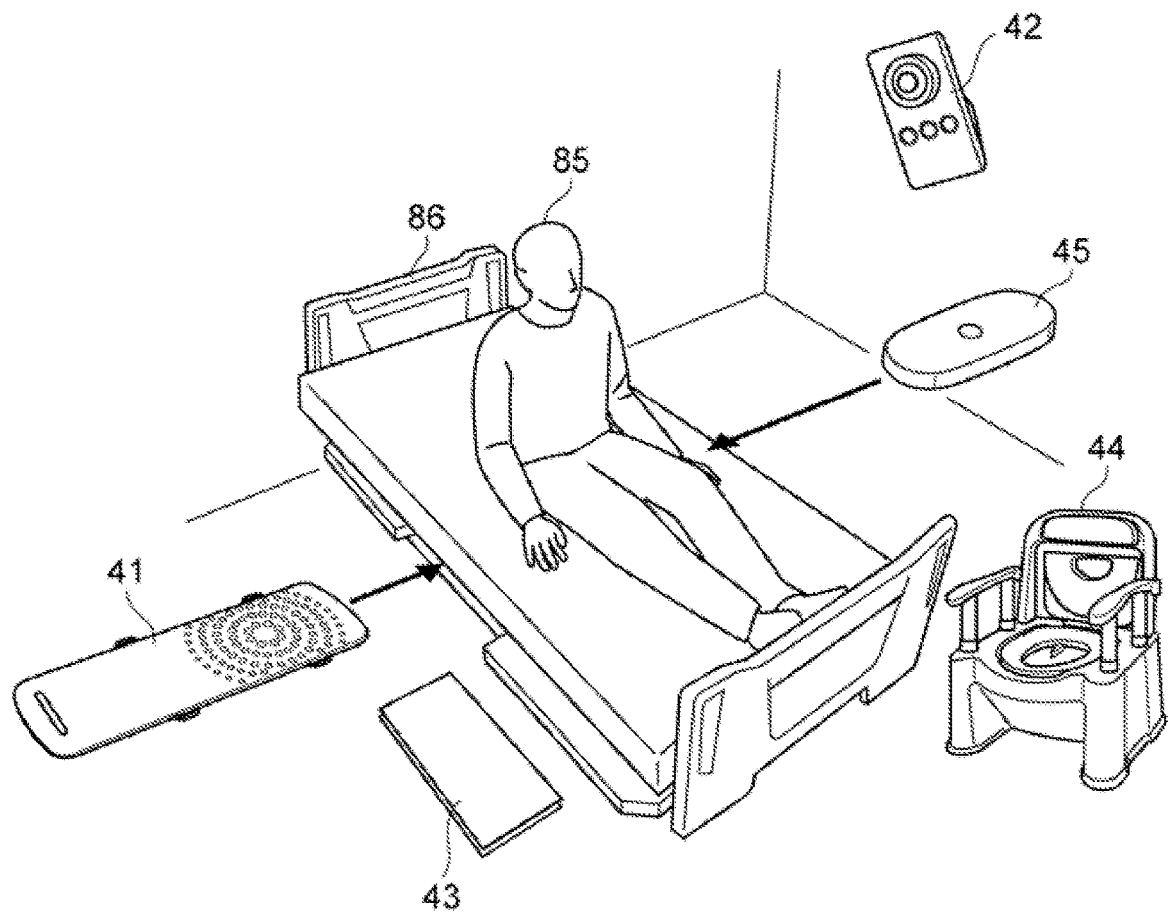
FIG. 2 is an exemplary schematic diagram illustrating the data processor according to the first embodiment.

FIG. 2 is an exemplary schematic diagram illustrating a data processor according to the first embodiment.

As illustrated in FIG. 2, the sensor is used together with a bed 86 that is used by a human subject 85 (for example, a care receiver), for example. The sensor may include, for example, at least any of a body movement sensor 41, an imaging device 42, a weighted sensor 43, an excretion device 44, and an excretion sensor 45.

The body movement sensor 41 is provided to the bed 86 that is used by the human subject 85, for example. The body movement sensor 41 is provided between sections and a mattress of the bed 86, for example. The body movement sensor 41 is configured to detect vibration or the like with the body movement by the human subject 85, for example.

The imaging device 42 is configured to imaging the human subject 85. The imaging device 42 may be configured to image a space including the bed 86 that is used by the human subject 85, for example. For example, the imaging device 42 is configured to image the human subject 85 on the bed 86. The imaging device 42 may be configured to image the human subject 85 who is distant from the bed 86.

The weighted sensor 43 is provided to a floor on which the bed 86 is placed, for example. For example, the weighted sensor 43 is configured to detect weighting from the human subject 85. The human subject 85 stands up from the bed 86, and moves onto the weighted sensor 43. At this time, the weighted sensor 43 detects weighting from the human subject 85. The weighted sensor 43 can detect bed-leaving by the human subject 85. The weighted sensor 43 is, for example, a bed-leaving sensor.

The excretion device 44 is a toilet bowl that is used by the human subject 85. The excretion device 44 is configured to detect excretion by the human subject 85.

The excretion sensor 45 may be provided onto the mattress of the bed 86, for example. The excretion sensor is configured to detect smell with the excretion, for example. The excretion sensor 45 is, for example, an odor sensor. The excretion sensor 45 is configured to detect the excretion by the human subject 85 based on the odor, for example. The excretion sensor 45 may be attached in a diaper of the human subject 85 for example. The excretion sensor 45 may be detect color or a change in color associated with the excretion. The excretion sensor 45 includes, for example, an image sensor. The excretion sensor 45 may detect the excretion of human subject 85 based on the color information or the change in color in the diaper of the human subject 85. In the embodiment, these sensors may be used in various combinations with one another.

In a first example, the first sensor 31 includes the body movement sensor 41. Meanwhile, the second sensor includes the excretion device 44 or the excretion sensor 45. In this case, the first event is excretion. Before the excretion by the human subject 85, for example, the body movement becomes large. By detecting the magnitude or the like of the body movement, the first event (excretion) can be predicted. For example, based on a temporal change or the like in the body movement, it is possible to detect whether the human subject 85 is in a hurry than usual. Information related to such the body movement serves as the first data DA1. In the embodiment, based on the first data DA1 obtained by the first sensor 31 (the body movement sensor 41), the first event prediction information IP1 on the first event (excretion) and the state prediction information SP1 (being in a hurry, the abnormal state such as the fall or the tumble) in the first event are predicted. The second sensor is configured to detect the excretion. The second sensor does not detect the state prediction information SP1 (being in a hurry, the abnormal state such as the fall or the tumble).

In a second example, the first sensor 31 includes the imaging device 42. Meanwhile, the second sensor includes the excretion device 44 or the excretion sensor 45. In this case, the first event is excretion. Information related to the magnitude of the body movement before the excretion by the human subject 85, and information related to a temporal change or the like in the body movement are obtained by the imaging device 42. In the second example as well, based on the first data DA1 obtained by the first sensor 31 (the imaging device 42), the first event prediction information IP1 on the first event (excretion) and the state prediction information SP1 (being in a hurry, the abnormal state such as the fall or the tumble) in the first event are predicted. The second sensor is configured to detect the excretion. The second sensor does not detect the state prediction information SP1 (being in a hurry, the abnormal state such as the fall or the tumble).

In a third example, the first sensor 31 includes the body movement sensor 41. Meanwhile, the second sensor includes the weighted sensor 43. In this case, the first event is bed-leaving. Before the bed-leaving by the human subject 85, for example, the body movement becomes large. By detecting the magnitude or the like of the body movement, the first event (bed-leaving) can be predicted. For example, based on a temporal change or the like in the body movement, it is possible to detect whether the human subject 85 is in a hurry than usual. Information related to such the body movement serves as the first data DA1. In the embodiment, based on the first data DA1 obtained by the first sensor 31 (the body movement sensor 41), the first event prediction information IP1 on the first event (bed-leaving) and the state prediction information SP1 (being in a hurry, the abnormal state such as the fall or the tumble) in the first event are predicted. The second sensor is configured to detect the bed-leaving. The second sensor does not detect the state prediction information SP1 (being in a hurry, the abnormal state such as the fall or the tumble).

In a fourth example, the first sensor 31 includes the imaging device 42. Meanwhile, the second sensor includes the weighted sensor 43. In this case, the first event is bed-leaving. Information related to the magnitude of the body movement before the bed-leaving by the human subject 85, and information related to a temporal change or the like in the body movement are obtained by the imaging device 42. Based on the first data DA1 obtained by the first sensor 31 (the imaging device 42), the first event prediction information IP1 on the first event (bed-leaving) and the state prediction information SP1 (being in a hurry, the abnormal state such as the fall or the tumble) in the first event are predicted. The second sensor is configured to detect the bed-leaving. The second sensor does not detect the state prediction information SP1 (being in a hurry, the abnormal state such as the fall or the tumble).

In the embodiment, the first sensor 31 may include at least either of the body movement sensor 41 provided to the bed 86 that is used by the human subject 85, and the imaging device 42 that images the human subject 85. For example, the second sensor may include at least either of the excretion device 44 that is used by the human subject and the excretion sensor 45 configured to detect the excretion by the human subject 85.

In another example, the first sensor 31 includes at least either of the body movement sensor 41 and the imaging device 42. The second sensor includes the weighted sensor 43 configured to detect weighting from the human subject 85.

The second sensor is, for example, a binary sensor that detects the presence or absence of the first event (bed-leaving, excretion, or the like). Meanwhile, the first sensor 31 is a multivalued sensor that continuously detects a state of the human subject 85. The first sensor 31 detects a change in the state of the human subject 85 that is generated before the occurrence of the first event. Based on a detection result of the change in the state of the human subject 85 by the first sensor 31, a prediction of the occurrence of the first event and the state of the human subject 85 (abnormal state) in the first event are predicted.

The second sensor is, for example, a "poor sensor". The first sensor 31 is, for example, a "rich sensor". By combining these sensors with each other, it is possible to detect the abnormal state of the human subject 85 more accurately. In the embodiment, various modifications of the combination of such the first sensor 31 and the second sensor are possible. As is described later, for example, the amount of information to be obtained from the first sensor 31 is larger than the amount of information to be obtained from the second sensor.

Hereinafter, an example of the derivation of the first event prediction information IP1 and the state prediction information SP1 will be described.

Figure 3A:
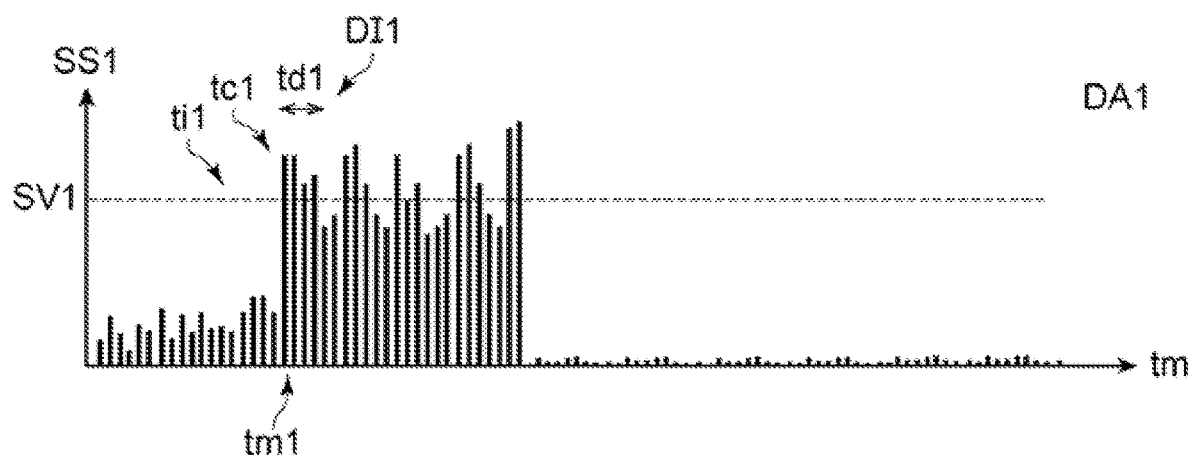
FIGS. 3A to 3C are exemplary schematic diagrams illustrating an operation of the data processor according to the first embodiment.
Figure 3B:
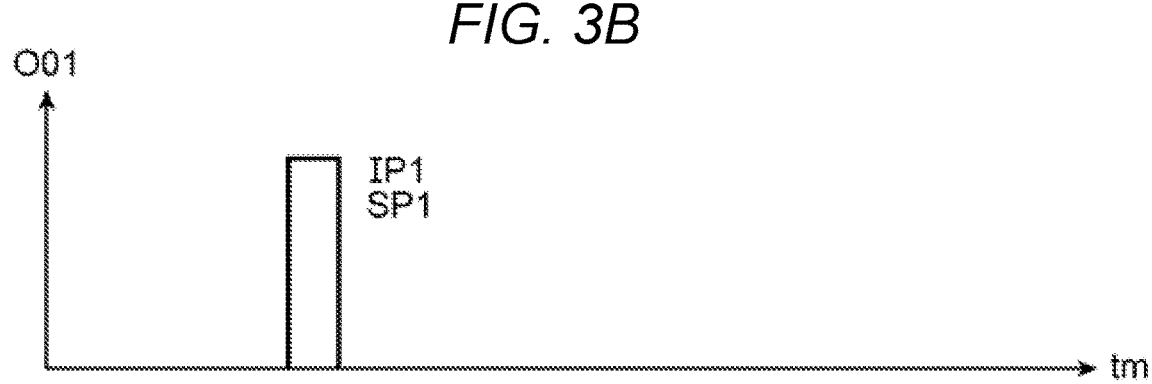
Figure 3C:
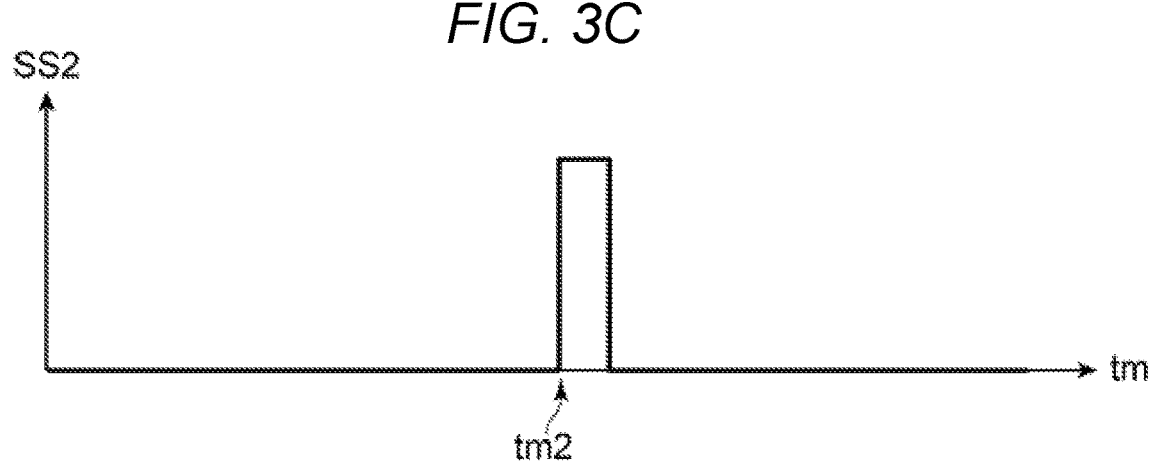

FIGS. 3A to 3C are exemplary schematic diagrams illustrating operations of the data processor according to the first embodiment.

The horizontal axis in each of these drawings represents time tm. The longitudinal axis in FIG. 3A represents signal intensity SS1 of signals that are detected by the first sensor 31. The signal intensity SS1 corresponds to the first data DA1, for example. The longitudinal axis in FIG. 3B represents signal intensity corresponding to output information OO1. FIG. 3B exemplifies output of the first event prediction information IP1 and the state prediction information SP1 from the processor 71. The longitudinal axis in FIG. 3C represents intensity SS2 of signals related to the occurrence of the first event that is detected by the second sensor.

As illustrated in FIG. 3C, at time tm2, the occurrence of the first event that is detected by the second sensor is detected. For example, the second sensor detects bed-leaving, excretion, or the like, at the time tm2.

The first data DA1 that is exemplified in FIG. 3A is supplied to the processor 71. As illustrated in FIG. 3A, the signal intensity SS1 of signals that are detected by the first sensor 31 changes with the time tm. The signal intensity SS1 corresponds to the magnitude of the body movement, for example. For example, as for the signal intensity SS1, a first threshold SV1 is set. For example, the processor 71 detects a state ti1 in which the signal intensity SS1 exceeds the first threshold SV1. For example, the processor 71 may detect a frequency tc1 of the state ti1 in which the signal intensity SS1 exceeds the first threshold SV1. For example, the processor 71 may detect occurrence time tm1 of the state ti1 in which the signal intensity SS1 exceeds the first threshold SV1. For example, the processor 71 may detect duration time td1 of the state ti1 in which the signal intensity SS1 exceeds the first threshold SV1. The processor 71 is configured to derive the first event prediction information IP1 and the state prediction information SP1, based on these detection results.

For example, when the duration time td1 is longer than a second threshold, the first event (for example excretion or the like) can be predicted. When the duration time td1 is longer than the second threshold, and the frequency tc1 is higher than a third threshold, it can be predicted that the human subject performs the first event (for example, excretion) in a hurry. This derives the first event prediction information IP1 and the state prediction information SP1. The state prediction information SP1 includes, for example, an abnormal state. The abnormal state includes, for example, being in a hurry, a higher possibility of the fall and the tumble than usual, or the like.

The first data information DI1 related to the first data DA1 may include at least any of the state ti1 in which the signal intensity SS1 corresponding to the body movement by the human subject 85 exceeds the first threshold SV1, the frequency tc1 of the state ti1, the occurrence time tm1 of the state ti1, and the duration time td1 of the state ti1. When the first data DA1 includes such the first data information DI1, the processor 71 derives the first event prediction information IP1 and the state prediction information SP1, in accordance with the first data information DI1. The occurrence time tm1 of the state ti1 is prior to the time tm2 at the occurrence of the first event that is detected by the second sensor.

As illustrated in FIG. 3B, the processor 71 outputs the first event prediction information IP1 and the state prediction information SP1 prior to the time tm2 at the occurrence of the first event that is detected by the second sensor.

The first event prediction information IP1 and the state prediction information SP1 are supplied to the user via the terminal device 81. The user performs appropriate processing based on the information.

Such the operation of the processor 71 can be conducted by machine learning, for example. Hereinafter, an example of the machine learning of the processor 71 according to the embodiment will be described.

Figure 4:
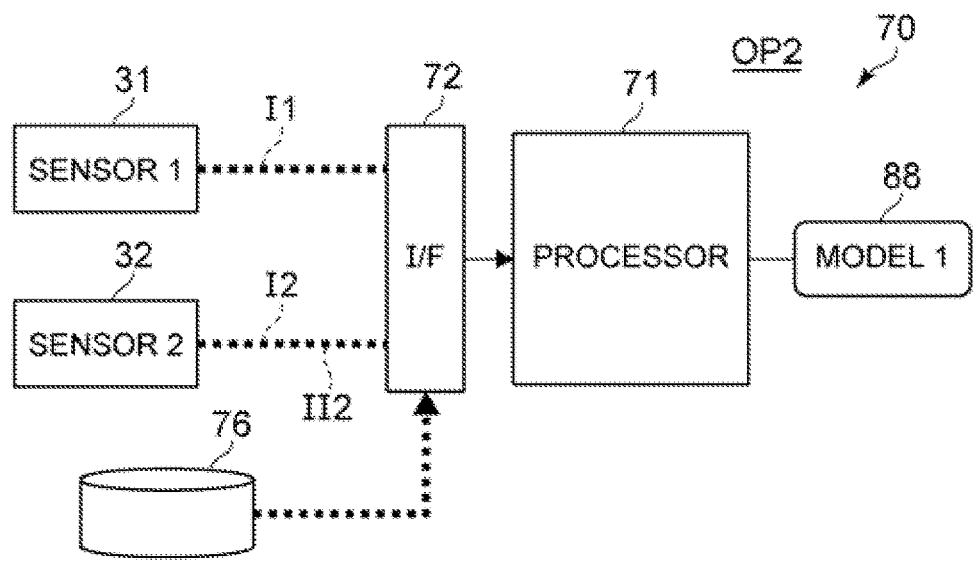
FIG. 4 is an exemplary schematic diagram illustrating the operation of the data processor according to the first embodiment.

FIG. 4 is an exemplary schematic diagram illustrating an operation of the data processor according to the first embodiment.

FIG. 4 exemplifies a second operation OP2 in the data processor 70. The second operation OP2 is an operation in a machine learning mode. At least a part of the second operation OP2 is conducted before the first operation OP1.

The processor 71 is configured to acquire first information I1 that is obtained from the first sensor 31, and second information I2 that is obtained from a second sensor 32, in the second operation OP2. The information may be supplied to the processor 71 via the acquisitor 72. The information may be stored in the memory 76, and the information stored in the memory 76 may be supplied to the processor 71.

The processor 71 is configured to derive a machine learning model 88 based on the first information I1 and the second information I2. The processor 71 is configured to conduct the first operation OP1 based on the machine learning model 88. The machine learning model 88 may include, for example, various kinds of functions such as a polynomial expression.

Hereinafter, an example of processing in the processor 71 in the second operation OP2 will be described.

Figure 5A:
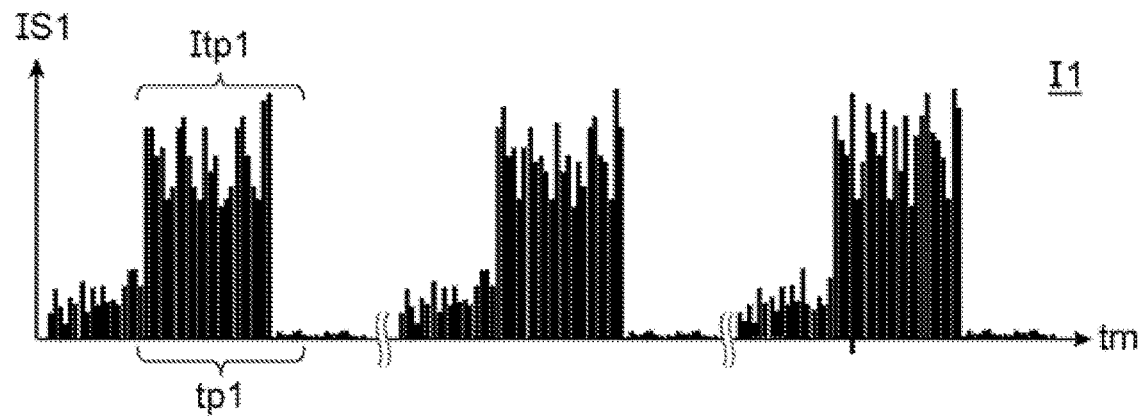
FIGS. 5A and 5B are exemplary schematic diagrams illustrating the operation of the data processor according to the first embodiment.
Figure 5B:
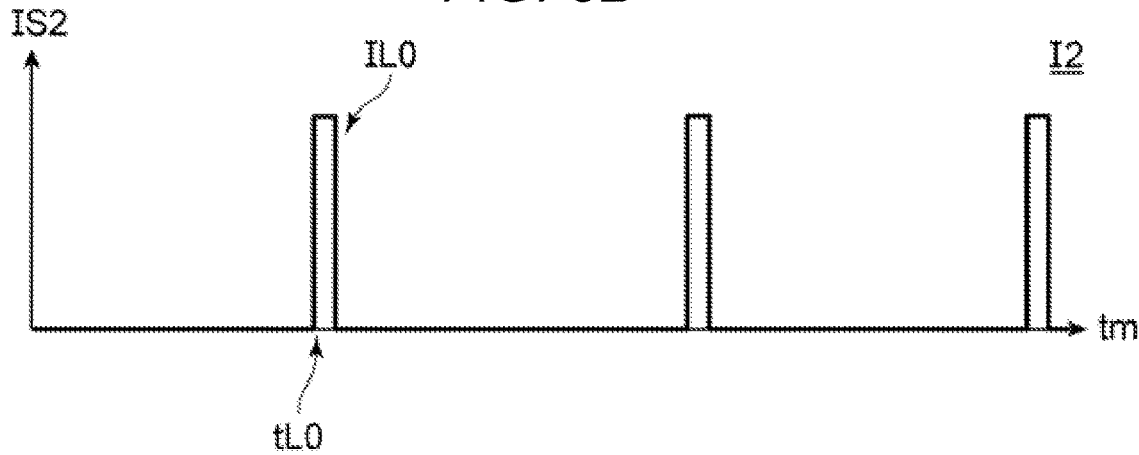

FIGS. 5A and 5B are exemplary schematic diagrams illustrating the operation of the data processor according to the first embodiment.

The horizontal axis in each of these drawings represents time tm. The longitudinal axis in FIG. 5A represents signal intensity IS1 of signals that are detected by the first sensor 31. The signal intensity IS1 corresponds to the first information I1, for example. The longitudinal axis in FIG. 5B represents intensity IS2 of signals that are detected by the second sensor 32 and related to the occurrence of a learning-time event.

The first sensor 31 is, for example, a multivalued sensor that continuously detects a state of the human subject 85. The second sensor 32 is a binary sensor that detects the presence or absence of the first event (bed-leaving, excretion, or the like). The amount of the first information I1 is larger than the amount of the second information I2.

As illustrated in FIG. 5B, the second information I2 includes learning-time event occurrence information IL0 related to the occurrence of a learning-time event. The learning-time event corresponds to the abovementioned first event. The second sensor 32 detects the occurrence of the learning-time event. When the first event is bed-leaving, the learning-time event is bed-leaving at the time of learning. When the first event is excretion, the learning-time event is excretion at the time of learning. The learning-time event occurrence information IL0 includes information related to having detected the occurrence of bed-leaving, excretion, or the like. The occurrence of the learning-time event is performed at time tL0, for example.

As illustrated in FIG. 5A, the first information I1 includes first period information Itp1. The first period information Itp1 is obtained from the first sensor 31 during a first period tp1. The first period tp1 includes a period prior to the occurrence of the learning-time event (time tL0).

The first sensor 31 continuously detects a state of the human subject 85. The first information I1 that is obtained from the first sensor 31 includes information prior to the occurrence of the learning-time event (time tL0). For example, the processor 71 may extract, from the continuous first information I1, information during the first period tp1 prior to the occurrence of the learning-time event (time tL0).

The first period information Itp1 corresponding to the first period tp1 is used as part of training data in the machine learning. The first period information Itp1 is, for example, an explanatory variable.

The learning-time event occurrence information IL0 related to the occurrence of the learning-time event is used as part of training data in the machine learning. The learning-time event occurrence information IL0 is, for example, an objective variable.

The processor 71 is configured to derive the machine learning model 88 using the learning-time event occurrence information IL0 and information based on the first period information Itp1 as training data, in the second operation OP2.

In the first operation OP1, by inputting the machine learning model 88 derived in the second operation OP2 into the first data DA1, the occurrence of the first event can be predicted.

The processor 71 adds, for example, a first annotation to the first period information Itp1, based on the learning-time event occurrence information IL0, in the second operation OP2. For example, the training data includes the first period information Itp1 to which the first annotation has been added.

For example, the first period tp1 is a period including a period before the time tL0 at the occurrence of the learning-time event. This period may be set in advance. The first annotation related to the presence or absence of the learning-time event is added to the first period information Itp1 during the first period tp1. The processor 71 may perform addition of the first annotation. The processor 71 that is included in the data processor 70 performs the addition of the annotation, so that the machine learning can be efficiently conducted at high speed.

As mentioned above, the processor 71 is configured to conduct the first operation OP1 based on the first data DA1 acquired by the acquisitor 72. At least a part of the first data DA1 is obtained from the first sensor 31. In the embodiment, the part of the first data DA1 may be obtained from another sensor (for example, a third sensor).

Figure 6:
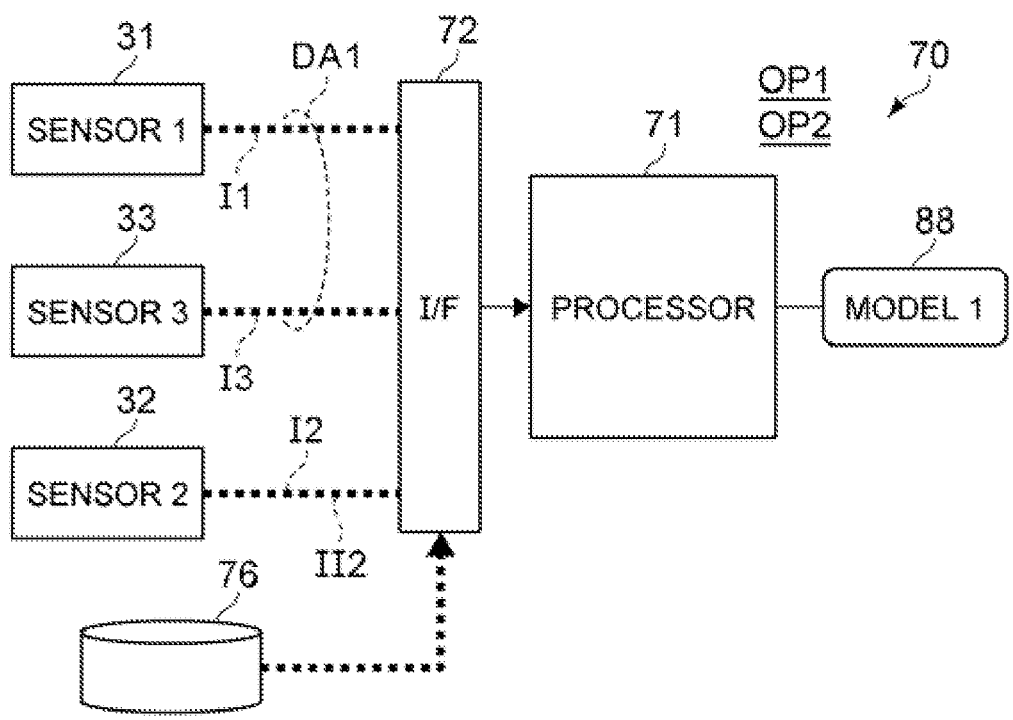
FIG. 6 is an exemplary schematic diagram illustrating the operation of the data processor according to the first embodiment.

FIG. 6 is an exemplary schematic diagram illustrating an operation of the data processor according to the first embodiment.

As illustrated in FIG. 6, part of the first data DA1 may be obtained from a third sensor 33 configured to detect a state of the human subject 85.

In one example, the first sensor 31 includes the body movement sensor 41 provided to the bed that is used by the human subject 85. The third sensor 33 includes the imaging device 42 that images the human subject 85. The second sensor 32 includes at least either of the excretion device 44 that is used by the human subject 85 and the excretion sensor 45 configured to detect excretion by the human subject 85. The first data DA1 including a detection result by the first sensor 31 and a detection result by the third sensor 33 are input into the machine learning model 88. This causes the first event prediction information IP1 and the state prediction information SP1 to be output. In this case, the first event includes excretion. The state at the occurrence of the first event includes, for example, a prediction of an abnormal state (at least any of being in a hurry, a fall, and a tumble).

In another example, the first sensor 31 includes the body movement sensor 41. The third sensor 33 includes the imaging device 42. The second sensor 32 includes the weighted sensor 43 configured to detect weighting from the human subject 85. In this case, the first event includes bed-leaving. The state at the occurrence of the first event includes, for example, a prediction of an abnormal state (at least any of being in a hurry, a fall, and a tumble).

For example, in the second operation OP2 (operation in the machine learning mode), information that is obtained from the third sensor 33 may be used.

As illustrated in FIG. 6, for example, in the second operation OP2, the processor 71 is configured to acquire the first information I1 that is obtained from the first sensor 31, the second information I2 that is obtained from the second sensor 32, and third information I3 that is obtained from the third sensor 33. The processor 71 is configured to derive the machine learning model 88 using information including the information as training data, in the second operation OP2. The processor 71 is configured to conduct the first operation OP1, based on the machine learning model 88.

Figure 7A:
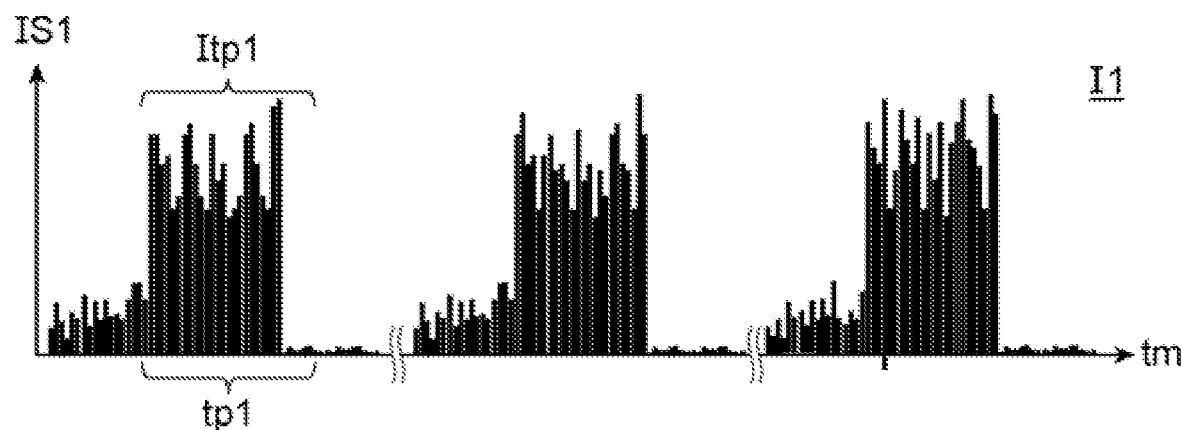
FIGS. 7A to 7C are exemplary schematic diagrams illustrating the operation of the data processor according to the first embodiment.
Figure 7B:
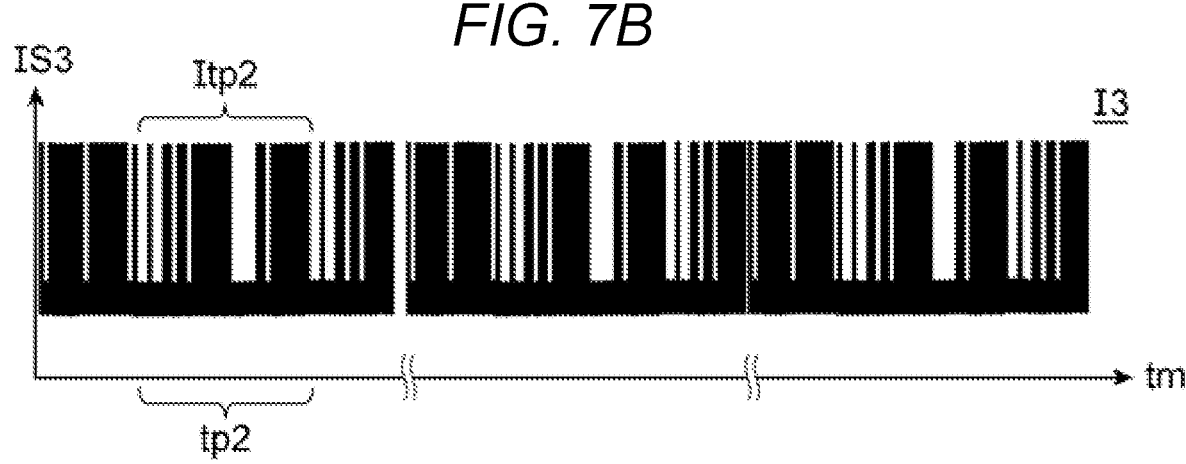
Figure 7C:
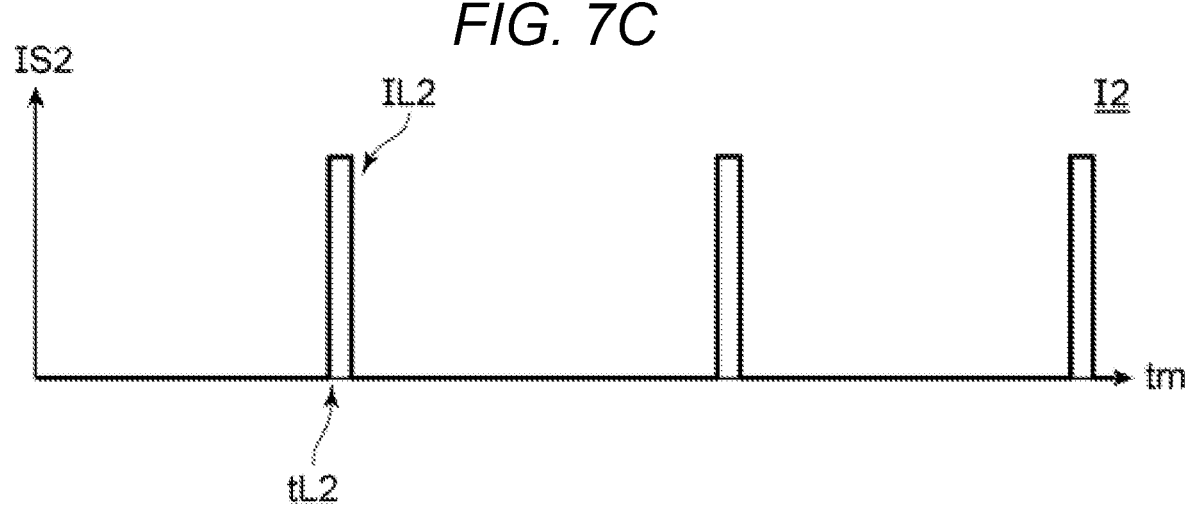

FIGS. 7A to 7C are exemplary schematic diagrams illustrating the operation of the data processor according to the first embodiment.

The horizontal axis in each of these drawings represents the time tm. The longitudinal axis in FIG. 7A represents the signal intensity IS1 of signals that are detected by the first sensor 31. The signal intensity IS1 corresponds to the first information I1, for example. The longitudinal axis in FIG. 7B represents signal intensity IS3 of signals (video signals may be used) that are detected by the third sensor 33. The signal intensity IS3 corresponds to the third information I3, for example. The longitudinal axis in FIG. 7C represents the intensity IS2 of signals that are detected by the second sensor 32 and related to the occurrence of the learning-time event.

The amount of the first information I1 is larger than the amount of the second information I2. In this example, the amount of the third information I3 is larger than the amount of the second information I2.

As illustrated in FIG. 7C, the second information I2 includes second event occurrence information IL2 related to an occurrence of a second event that is detected by the second sensor 32. The second event corresponds to the first event. The second event is an event at the time of machine learning. The second event is detected at time tL2.

As illustrated in FIG. 7A, the first information I1 includes the first period information Itp1. The first period information Itp1 includes information (at least a part of the first information I1) that is obtained from the first sensor 31 during the first period tp1 including a period prior to the occurrence of the second event (the time tL2).

As illustrated in FIG. 7B, the third information I3 includes second period information Itp2. The second period information Itp2 includes information (at least a part of the third information I3) that is obtained from the third sensor 33 during a second period tp2 including a period prior to the occurrence of the second event (the time tL2).

The processor 71 is configured to derive the machine learning model 88 (see FIG. 6) using the second event occurrence information IL2, the information based on the first period information Itp1, and information based on the second period information Itp2 as training data, in the second operation OP2. The processor 71 is configured to conduct the first operation OP1 based on the machine learning model 88.

The processor 71 may add the first annotation to the first period information Itp1, and may add a second annotation to the second period information Itp2, based on the second event occurrence information IL2, in the second operation OP2. The training data includes, for example, the first period information Itp1 to which the first annotation has been added, and the second period information Itp2 to which the second annotation has been added.

The first information I1 that is obtained from the first sensor 31, and the third information I3 that is obtained from the third sensor 33 are used, so that the first event prediction information IP1 can be derived more accurately, for example. The first information I1 and the third information I3 are used, so that the state prediction information SP1 can be derived more accurately, for example. The first information I1 and the third information I3 are used, so that the type of the state prediction information SP1 is increased, for example.

For example, a plurality of types of information (the first information I1, the third information I3, and the like) that are obtained from the different sensors (the first sensor 31 and the third sensor 33) are used, so that an abnormal state can be derived more accurately, for example.

Figure 8A:
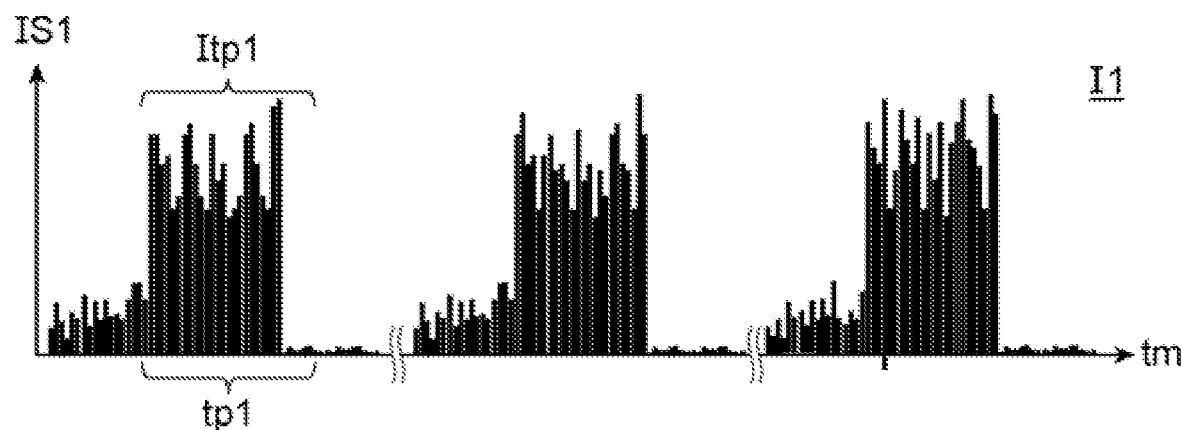
FIGS. 8A to 8C are exemplary schematic diagrams illustrating the operation of the data processor according to the first embodiment.
Figure 8B:
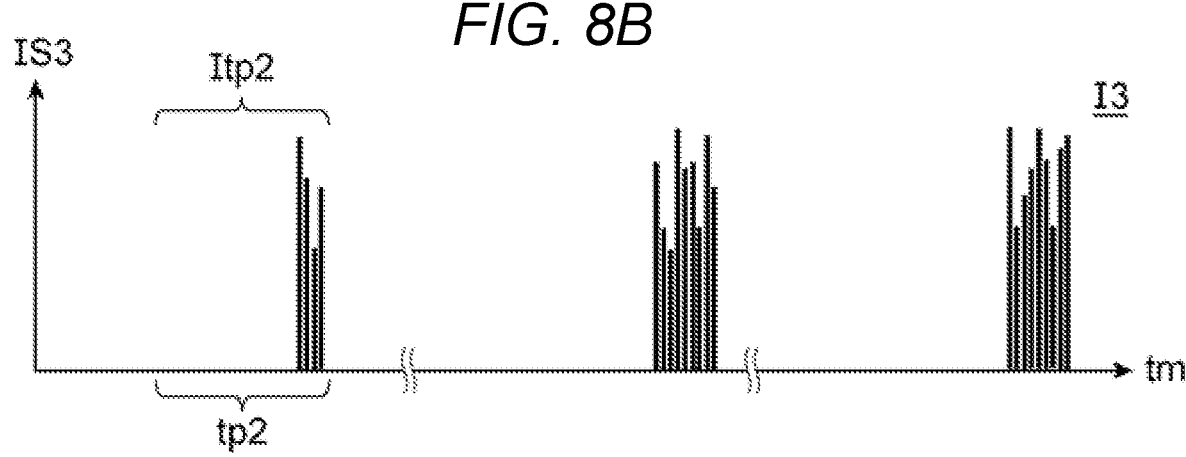
Figure 8C:
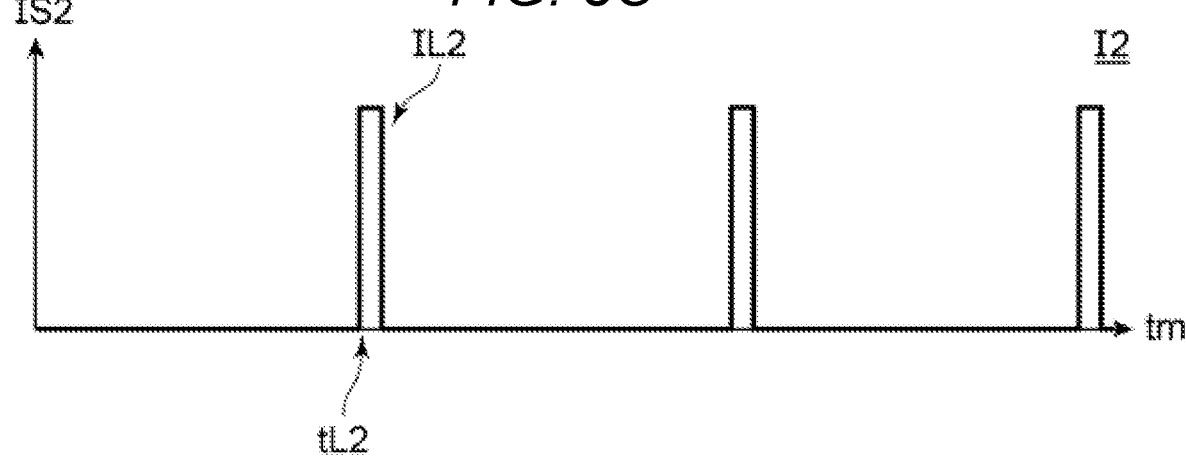

FIGS. 8A to 8C are exemplary schematic diagrams illustrating the operation of the data processor according to the first embodiment.

The horizontal axis in each of these drawings represents the time tm. The longitudinal axis in FIG. 8A represents the signal intensity IS1 of signals that are detected by the first sensor 31. The signal intensity IS1 corresponds to the first information I1, for example. In the example of FIG. 8A, the first sensor 31 includes the body movement sensor 41. The longitudinal axis in FIG. 8B represents the signal intensity IS3 of signals that are detected by the third sensor 33. The signal intensity IS3 corresponds to the third information I3, for example. In the example of FIG. 8B, the third sensor 33 includes the weighted sensor 43. The longitudinal axis in FIG. 8C represents the intensity IS2 of signals that are detected by the second sensor 32 and related to the occurrence of the learning-time event. In the example of FIG. 8C, the second sensor 32 includes the excretion device 44.

In the examples of FIGS. 8A to 8C, the first sensor 31 detects the time (the duration time td1) of the body movement that exceeds a threshold. The third sensor 33 can detect the time from the bed-leaving to when walking is started. The second sensor 32 detects excretion. In this example, when the time from the bed-leaving to when walking is started is longer than a threshold (normal value), the processor 71 outputs the state prediction information SP1 related to an abnormal state. The abnormal state includes, for example, at least any of a state of being in a hurry, a fall, and a tumble.

As mentioned above, the processor 71 may output the first event prediction information IP1 and the state prediction information SP1, based on the first data DA1 that is obtained by the plurality of the sensors (the first sensor 31 and the third sensor 33).

In the examples of FIGS. 8A to 8C, for example, the second period tp2 may be on and after the first period tp1. The second period tp2 may be after the first period tp1. Information (at least a part of the third information I3) may be obtained from the third sensor 33, during the second period tp2 after the first period tp1 during when information (at least a part of the first information I1) is obtained from the first sensor 31.

In the embodiment, the processor 71 may provide an annotation based on the information from the plurality of the sensors (the first sensor 31 and the third sensor 33). Acquisition periods (for example, the first period tp1 and the second period tp2) of data that is used when the annotation is provided can be preferably changed (designated).

For example, when an event is predicted based on the plurality of the sensors (the first sensor 31 and the third sensor 33), a prediction period in one of the plurality of the sensors and a prediction period in the other of the plurality of the sensors are different from each other in some cases. The different periods can be designated to enable a more accurate prediction.

When an event is predicted based on the plurality of the sensors (the first sensor 31 and the third sensor 33), spatial positions in the detection by the plurality of the sensors may be different from each other. For example, an exercise (for example, a walk) by the human subject 85, and a state (for example, the temperature and the humidity) in a room of the human subject 85, may be detected by the plurality of the sensors. In this case, places of the detection by the plurality of the sensors are different from each other. In such a case, the processor 71 may provide an annotation based on the information that is obtained from the plurality of the sensors (the first sensor 31 and the third sensor 33). The detection place of data that is used when the annotation is provided can be preferably changed (designated). The more accurate prediction is enabled.

In the embodiment, a plurality of events may be predicted. For example, the acquisitor 72 is configured to acquire the first data DA1. The processor 71 may be configured to conduct the first operation OP1 based on the first data DA1 acquired by the acquisitor 72. At least a part of the first data DA1 is obtained from the first sensor 31 configured to detect a state of the human subject 85. The processor 71 may be configured to output, when the first data DA1 includes the first data information DI1, the first event prediction information IP1 related to the occurrence of the first event related to the human subject 85, and second event prediction information related to the occurrence of the second event after the first event, in the first operation OP1. The second sensor 32 configured to detect a state of the human subject 85 is configured to detecting the occurrence of the first event. The third sensor 33 configured to detect a state of the human subject 85 is configured to detect the occurrence of the second event.

For example, the first event includes bed-leaving. The second event includes excretion. In this example, the first sensor 31 is the body movement sensor 41. Based on the data that is obtained by the first sensor 31, bed-leaving is predicted as the first event, and excretion is predicted as the second event. For example, a plurality of chained events may be predicted.

As for the plurality of the events, the processor 71 may provide an annotation. For example, when the second sensor 32 detects excretion, an annotation may be provided to information that is obtained from the first sensor 31, and an annotation may be further provided to information that is obtained from the third sensor 33. For example, based on the results, a state prediction is performed more appropriately.

For example, based on a detection result by the second sensor 32, an annotation is provided to each of detection results by the plurality of the sensors (the first sensor 31 and the third sensor 33). For example, when duration time of the large body movement is longer than a threshold (normal value) as well, the state prediction information SP1 related to the abnormal state is output.

For example, the first sensor 31 includes the body movement sensor 41 provided to the bed 86 that is used by the human subject 85. The second sensor 32 includes the weighted sensor 43 configured to detect weighting from the human subject 85. The third sensor 33 includes at least either of the excretion device 44 that is used by the human subject 85 and the excretion sensor 45 configured to detect excretion by the human subject 85.

FIG. 9A to FIG. 9D are exemplary schematic diagrams illustrating sensors that are used in the data processor according to the first embodiment.

Figure 9A:
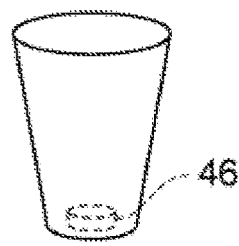
FIG. 9A to FIG. 9D are exemplary schematic diagrams illustrating sensors that are used in the data processor according to the first embodiment.

As illustrated in FIG. 9A, a sensor that is used by the data processor 70 may include a moisture sensor 46. The moisture sensor 46 is configured to detect water that is taken by the human subject 85. The moisture sensor 46 may be provided to a beverage container or the like that is used by the human subject 85, for example. The moisture sensor 46 may detect, for example, the weight, the height of a liquid surface, or the like, and may be configured to detect the amount of water that is taken by the human subject 85, based on the result. The moisture sensor 46 may be, for example, a device that manages the water to be taken by the human subject 85.

Figure 9B:
Figure 9B:
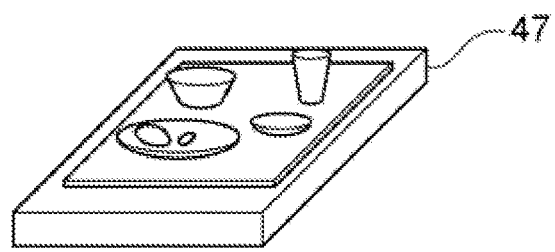

As illustrated in FIG. 9B, a sensor that is used by the data processor 70 may include an eating-and-drinking sensor 47. The eating-and-drinking sensor 47 is configured to detect eating and drinking by the human subject 85. The eating-and-drinking sensor 47 may be configured to detect, for example, an amount (weight) of a meal that is taken by the human subject 85. The eating-and-drinking sensor 47 may include, for example, a measuring instrument for weight. The eating-and-drinking sensor 47 may include, for example, an imaging element 47a. The amount of the meal may be detected from an image by the imaging element 47a.

Figure 9C:
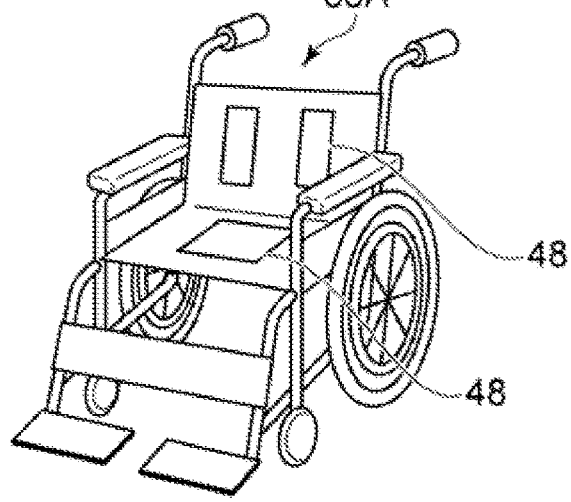

As illustrated in FIG. 9C, a sensor that is used by the data processor 70 may include a posture sensor 48. The posture sensor 48 is configured to detect a posture of the human subject 85. The posture sensor 48 may detect, for example, weighting by the human subject 85. The posture sensor 48 may be configured to optically detect, for example, a posture of the human subject 85. In this example, the posture sensor 48 is provided to a wheelchair 86A. The posture sensor 48 may be provided at an arbitrary place.

Figure 9D:

As illustrated in FIG. 9D, a sensor that is used by the data processor 70 may include a swallowing sensor 49. The swallowing sensor 49 is configured to detect a state of swallowing by the human subject 85. The swallowing sensor 49 may be configured to detect, for example, sound in the swallowing by the human subject 85. A state of the swallowing is detected based on a detection result of the sound. When the detected sound is different from the normal one, abnormal swallowing can be determined. The swallowing sensor 49 is configured to detect abnormal swallowing by the human subject 85. The swallowing sensor 49 may be attached to, for example, a cervical region or the like of the human subject 85. In the swallowing sensor 49, a swallowing state may be detected by an arbitrary method.

The sensor that is used by the data processor 70 may include at least any of the body movement sensor 41, the imaging device 42, the weighted sensor 43, the excretion device 44, the excretion sensor 45, the moisture sensor 46, the eating-and-drinking sensor 47, the posture sensor 48, and the swallowing sensor 49, for example.

In one example, the first event includes at least any of water intake, body movement, and excretion. A state to be predicted of the human subject 85 at the occurrence of the first event includes a prediction of incontinence. The state prediction information SP1 includes a prediction of the first event (at least any of water intake, body movement, and excretion), which is different from the normal one. For example, the state prediction information SP1 may include information related to at least any of water intake different from the normal one, body movement different from the normal one, and excretion different from the normal one. In this example, the first sensor 31 includes at least either of the body movement sensor 41 provided to the bed 86 that is used by the human subject 85, and the moisture sensor 46 configured to detect water intake by the human subject 85. For example, the second sensor 32 includes at least either of the excretion device 44 that is used by the human subject 85, and the excretion sensor 45 configured to detect excretion by the human subject 85.

In another example, the first event includes at least any of eating and drinking, body movement, and a change in a posture. For example, a state to be predicted of the human subject 85 at the occurrence of the first event includes a prediction of aspiration. The state prediction information SP1 includes a prediction of the first event (at least any of eating and drinking, body movement, and a change in a posture), which is different from the normal one. In this example, the first sensor 31 includes at least any of the body movement sensor 41 provided to the bed that is used by the human subject 85, the eating-and-drinking sensor 47 configured to detect eating and drinking by the human subject 85, and the posture sensor 48 configured to detect a posture of the human subject 85. The second sensor 32 includes the swallowing sensor 49 configured to detect abnormal swallowing by the human subject 85.

In the examples in which the various kinds of the sensors exemplified in FIG. 9A to FIG. 9D are used as well, the various kinds of processing having been described related to FIGS. 3 to 8 can be applied.

Figure 10:
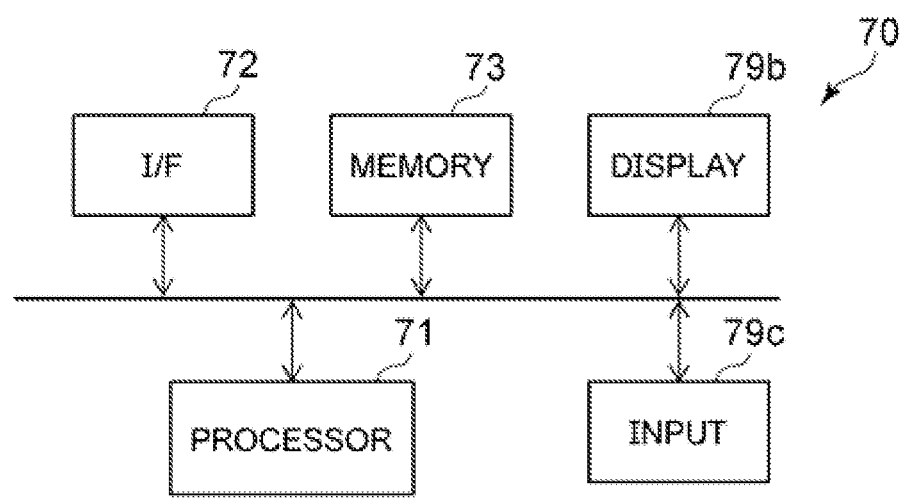
FIG. 10 is an exemplary schematic diagram illustrating the data processor according to the first embodiment.

FIG. 10 is an exemplary schematic diagram illustrating a data processor according to a first embodiment.

As illustrated in FIG. 10, the data processor 70 includes, for example, the processor 71, the acquisitor 72, and a memory 73. The processor 71 is, for example, an electric circuit. The memory 73 may include at least either of a read only memory (ROM) and a random access memory (RAM), for example. As the memory 73, an arbitrary storage device may be used.

The data processor 70 may include a display 79b, an input part 79c, and the like. The display 79b may include various kinds of displays. The input part 79c includes, for example, a device (for example, a keyboard, a mouse, a touch type input panel, or a sound recognition input device) including an operation function.

The embodiment may include a program. The program causes a computer (the processor 71) to conduct the abovementioned operations. The embodiment may include a storage medium in which the abovementioned program is stored.

Second Embodiment

Figure 11:
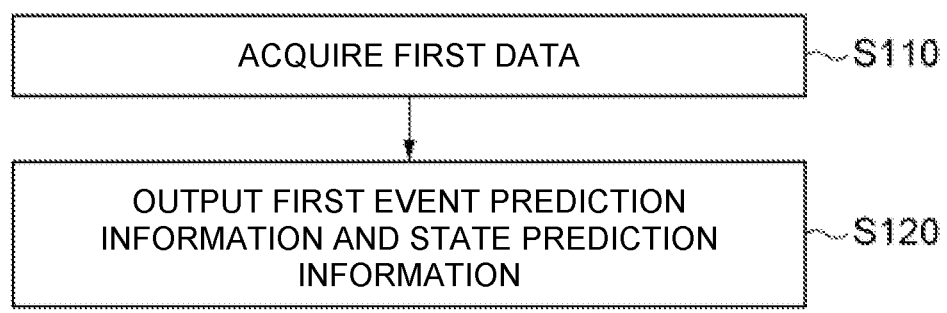
FIG. 11 is an exemplary flowchart illustrating a data processing method according to a second embodiment.

FIG. 11 is an exemplary flowchart illustrating a data processing method according to a second embodiment.

As illustrated in FIG. 11, a data processing method according to the embodiment causes the processor 71 to acquire the first data DA1 (Step S110). The data processing method causes the processor 71 to conduct the first operation OP1 based on the first data DA1. At least a part of the first data DA1 is obtained from the first sensor 31 configured to detect a state of the human subject 85.

The processor 71 is configured to output the first event prediction information IP1 and the state prediction information SP1, when the first data DA1 includes the first data information DI1, in the first operation OP1 (Step S120). The first event prediction information IP1 relates to an occurrence of the first event related to the human subject 85. The state prediction information SP1 relates to a state to be predicted of the human subject 85 at the occurrence of the first event. The second sensor 32 configured to detect a state of the human subject 85 is configured to detect the occurrence of the first event. The second sensor 32 does not detect a state to be predicted of the human subject 85 at the occurrence of the first event. In the data processing method according to the embodiment, the first operation OP1 that has been described as for the first embodiment can be conducted. In the data processing method according to the embodiment, the second operation OP2 that has been described as for the first embodiment can be conducted.

The embodiments may include the following configurations.

(Configuration 1)

A data processor comprising:
an acquisitor configured to acquire a first data; and
a processor configured to conduct a first operation based on the first data acquired by the acquisitor,
at least a part of the first data being obtained from a first sensor configured to detect a state of a human subject,
the processor being configured to output, if the first data includes a first data information, a first event prediction information related to an occurrence of a first event related to the human subject, and a state prediction information related to a state to be predicted of the human subject at the occurrence of the first event, in the first operation, the occurrence of the first event being configured to be detected by a second sensor configured to detect the state of the human subject, and the state to be predicted of the human subject at the occurrence of the first event being configured not to be detected by the second sensor.

(Configuration 2)

The data processor according to configuration 1, wherein the first event includes at least one of bed-leaving or excretion, and the state to be predicted of the human subject at the occurrence of the first event includes a prediction including at least one of a fall or a tumble.

(Configuration 3)

The data processor according to configuration 2, wherein the state prediction information includes a prediction that the human subject performs the first event in a hurry.

(Configuration 4)

The data processor according to configuration 2 or 3, wherein the first sensor includes at least one of a body movement sensor provided to a bed to be used by the human subject, or an imaging device configured to images the human subject, and the second sensor includes at least one of an excretion device being used by the human subject, or an excretion sensor configured to detect excretion by the human (Configuration 5)

The data processor according to configuration 2 or 3, wherein the first sensor includes at least one of a body movement sensor provided to a bed to be used by the human subject, or an imaging device configured to image the human subject, and the second sensor includes a weighted sensor configured to detect weighting from the human subject.

(Configuration 6)

The data processor according to configuration 1, wherein the first event includes at least one of water intake, body movement, or excretion, and the state to be predicted of the human subject at the occurrence of the first event includes a prediction of incontinence.

(Configuration 7)

The data processor according to configuration 6, wherein the first event includes at least one of water intake, body movement, of excretion, and the state prediction information includes a prediction of the first event different from a normal event.

(Configuration 8)

The data processor according to configuration 6 or 7, wherein the first sensor includes at least one of a body movement sensor provided to a bed to be used by the human subject, or a moisture sensor configured to detect water intake by the human subject, and the second sensor includes at least one of an excretion device to be used by the human subject, and an excretion sensor configured to detect excretion by the human subject.

(Configuration 9)

The data processor according to configuration 1, wherein the first event includes at least one of eating-and-drinking, body movement, or a change in a posture, and the state to be predicted of the human subject at the occurrence of the first event includes a prediction of aspiration.

(Configuration 10)

The data processor according to configuration 9, wherein the state prediction information includes a prediction of the first event different from a normal event.

(Configuration 11)

The data processor according to configuration 9 or 10, wherein the first sensor includes at least one of a body movement sensor provided to a bed to be used by the human subject, an eating-and-drinking sensor configured to detect eating-and-drinking by the human subject, or a posture sensor configured to detect a posture of the human subject, and the second sensor includes a swallowing sensor configured to detect abnormal swallowing by the human subject.

(Configuration 12)

The data processor according to any one of configurations 2 to 11, wherein the first data information includes at least one of:
a state where signal intensity corresponding to the body movement by the human subject exceeds a first threshold;
a frequency of the state where the signal intensity exceeds the first threshold;
occurrence time of the state where the signal intensity exceeds the first threshold; or
duration time of the state where the signal intensity exceeds the first threshold.

(Configuration 13)

The data processor according to any one of configurations 1 to 12, wherein the processor is further configured to conduct a second operation, the processor is configured to acquire a first information obtained from the first sensor, and a second information obtained from the second sensor, in the second operation, an amount of the first information is larger than an amount of the second information, the second information includes a learning-time event occurrence information related to an occurrence of a learning-time event being detected by the second sensor, and the learning-time event corresponds to the first event, the first information includes a first period information obtained from the first sensor in a first period including a period prior to the occurrence of the learning-time event, the processor is configured to derive a machine learning model using the learning-time event occurrence information and an information based on the first period information, as training data, in the second operation, and the processor is configured to conduct the first operation, based on the machine learning model.

(Configuration 14)
The data processor according to configuration 13, wherein
the processor is configured to add a first annotation to the first period information, based on the learning-time event occurrence information, in the second operation, and
the training data includes the first period information to which the first annotation has been added.

(Configuration 15)
The data processor according to configuration 1, wherein
a part of the first data is obtained from a third sensor configured to detect the state of the human subject,
the first sensor includes a body movement sensor provided to a bed to be used by the human subject,
the third sensor includes an imaging device configured to image the human subject,
the second sensor includes at least one of an excretion device being used by the human subject, or an excretion sensor configured to detect excretion by the human subject,
the first event includes excretion, and
the state at the occurrence of the first event includes a prediction of at least one of a fall or a tumble.

(Configuration 16)
The data processor according to configuration 1, wherein
a part of the first data is obtained from a third sensor configured to detect the state of the human subject,
the first sensor includes a body movement sensor provided to a bed to be used by the human subject,
the third sensor includes an imaging device configured to image the human subject,
the second sensor includes a weighted sensor configured to detect weighting from the human subject,
the first event includes bed-leaving, and
the state at the occurrence of the first event includes a prediction of at least one of a fall or a tumble.

(Configuration 17)
The data processor according to configuration 15 or 16, wherein
the processor is further configured to conduct a second operation,
the processor is configured to acquire a first information obtained from the first sensor, a second information obtained from the second sensor, and a third information obtained from the third sensor, in the second operation,
an amount of the first information is larger than an amount of the second information,
the second information includes a second event occurrence information related to an occurrence of a second event detected by the second sensor, and the second event corresponds to the first event,
the first information includes a first period information obtained from the first sensor in a first period including a period prior to the occurrence of the second event,
the third information includes second period information obtained from the third sensor in a second period including a period prior to the occurrence of the second event,
the processor is configured to derive a machine learning model using the second event occurrence information, an information based on the first period information, and an information based on the second period information, as training data, in the second operation, and
the processor is configured to conduct the first operation, based on the machine learning model.

(Configuration 18)
The data processor according to configuration 17, wherein
the processor is configured to add a first annotation to the first period information, and add a second annotation to the second period information, based on the second event occurrence information, in the second operation, and
the training data includes the first period information to which the first annotation has been added, and the second period information to which the second annotation has been added.

(Configuration 19)
A data processor comprising:
an acquisitor configured to acquire a first data; and
a processor configured to conduct a first operation based on the first data acquired by the acquisitor,
at least a part of the first data being obtained from a first sensor configured to detect a state of a human subject,
the processor being configured to output, if the first data includes first data information, a first event prediction information related to an occurrence of a first event related to the human subject, and a second event prediction information related to an occurrence of a second event after the first event, in the first operation,
the occurrence of the first event being configured to detected by a second sensor configured to detect the state of the human subject, and
the occurrence of the second event being detected by a third sensor configured to detect the state of the human subject.

(Configuration 20)
The data processor according to configuration 19, wherein
the first event includes bed-leaving, and
the second event includes excretion.

(Configuration 21)
The data processor according to configuration 19 or wherein
the first sensor includes a body movement sensor provided to a bed to be used by the human subject,
the second sensor includes a weighted sensor configured to detect weighting from the human subject, and
the third sensor includes at least one of an excretion device to be used by the human subject, or an excretion sensor configured to detect excretion by the human subject.

(Configuration 22)
A care support system comprising:
the data processor according to configuration 1;
the first sensor; and
a terminal device,
the terminal device including an output part, and
the output part being configured to output the first event prediction information and the state prediction information.

(Configuration 23)
A data processing method comprising:
causing a processor to acquire a first data; and
causing the processor to conduct a first operation based on the first data,
at least a part of the first data being obtained from a first sensor configured to detect a state of a human subject,
the processor being configured to output, if the first data includes first data information, a first event prediction information related to an occurrence of a first event related to the human subject, and a state prediction information related to a state to be predicted of the human subject at the occurrence of the first event, in the first operation, the occurrence of the first event being configured to be detected by a second sensor configured to detect the state of the human subject, and the state to be predicted of the human subject at the occurrence of the first event being configured not to be detected by the second sensor.

With the embodiments, a data processor, a care support system, and a data processing method that allow more suitable processing can be provided.

In the foregoing, the embodiments of the invention have been described with reference to the specific examples. However, the invention is not limited to these specific examples. For example, the specific configurations of respective elements such as the processor and the acquisitor, which are included in the data processor, can be included in the scope of the invention, as long as those skilled in the art can similarly implement the invention by the appropriate selection from the publicly known range, and obtain the similar effects.

The combination of any two or more elements in the specific examples within a technically possible range is included in the scope of the invention as long as the gist of the invention is included.

In addition, all the data processors, the care support systems, and the data processing methods that can be implemented through the design changes as appropriate by those skilled in the art based on the data processor, the care support system, and the data processing method described above as the embodiments belong to the scope of the invention as long as the gist of the invention is included.

In addition, within the spirit of the invention, those skilled in the art can conceive of various changes and modifications, and it is understood that these changes and modifications also belong to the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A data processor comprising:

an acquisitor configured to acquire a first data corresponding to detected signals acquired from a first sensor and a second data acquired from a second sensor, the first sensor being different from the second sensor; and a processor, in response to the first data being acquired by the acquisitor, configured to conduct a first operation and a second operation based on the first data and the second data acquired by the acquisitor, at least a part of the first data being obtained from a first sensor configured to detect a state of a human subject, the processor being configured to output and provide for display, in response to the first data including a first data information corresponding to signal intensity of the detected signals acquired first data exceeding a first threshold, an occurrence of a first event prediction information related to an occurrence of a first event related to the human subject and a physical state prediction information related to a physical state to be predicted of the human subject at the occurrence of the first event, in the first operation, the first event being a physical activity of the human subject, the occurrence of the first event being configured to be detected by the second sensor configured to detect the state of the human subject based on the second data, and the physical state to be predicted of the human subject at the occurrence of the first event being configured not to be detected by the second sensor, the processor being configured to add an annotation data to the second data, the annotation data being generated based on the first event prediction information and the physical state prediction information, and to generate a machine learning model for the second operation based on the second data and the annotation data, wherein the processor is configured to conduct the first operation based on the machine learning model.

2. The data processor according to claim 1, wherein the first event includes at least one of bed-leaving or excretion, and the state to be predicted of the human subject at the occurrence of the first event includes a prediction including at least one of a fall or a tumble.

3. The data processor according to claim 2, wherein the state prediction information includes a prediction that the human subject performs the first event in a hurry.

4. The data processor according to claim 2, wherein the first sensor includes at least one of a body movement sensor provided to a bed to be used by the human subject, or an imaging device configured to images the human subject, and the second sensor includes at least one of an excretion device being used by the human subject, or an excretion sensor configured to detect excretion by the human subject.

5. The data processor according to claim 2, wherein the first sensor includes at least one of a body movement sensor provided to a bed to be used by the human subject, or an imaging device configured to image the human subject, and the second sensor includes a weighted sensor configured to detect weighting from the human subject.

6. The data processor according to claim 1, wherein the first event includes at least one of water intake, body movement, or excretion, and the state to be predicted of the human subject at the occurrence of the first event includes a prediction of incontinence.

7. The data processor according to claim 6, wherein
the first event includes at least one of water intake, body movement, of excretion, and
the state prediction information includes a prediction of the first event different from a normal event.

8. The data processor according to claim 6, wherein
the first sensor includes at least one of a body movement sensor provided to a bed to be used by the human subject, or a moisture sensor configured to detect water intake by the human subject, and
the second sensor includes at least one of an excretion device to be used by the human subject, and an excretion sensor configured to detect excretion by the human subject.

9. The data processor according to claim 1, wherein
the first event includes at least one of eating-and-drinking, body movement, or a change in a posture, and
the state to be predicted of the human subject at the occurrence of the first event includes a prediction of aspiration.

10. The data processor according to claim 9, wherein the state prediction information includes a prediction of the first event different from a normal event.

11. The data processor according to claim 9, wherein
the first sensor includes at least one of a body movement sensor provided to a bed to be used by the human subject, an eating-and-drinking sensor configured to detect eating-and-drinking by the human subject, or a posture sensor configured to detect a posture of the human subject, and
the second sensor includes a swallowing sensor configured to detect abnormal swallowing by the human subject.

12. The first data information includes at least one of:
a state where signal intensity corresponding to the body movement by the human subject exceeds the first threshold;
a frequency of the state where the signal intensity exceeds the first threshold;
occurrence time of the state where the signal intensity exceeds the first threshold;
or
duration time of the state where the signal intensity exceeds the first threshold.

13. The data processor according to claim 1, wherein
the processor is configured to acquire a first information obtained from the first sensor, and a second information obtained from the second sensor, in the second operation,
an amount of the first information is larger than an amount of the second information,
the second information includes a learning-time event occurrence information related to an occurrence of a learning-time event being detected by the second sensor, and the learning-time event corresponds to the first event,
the first information includes a first period information obtained from the first sensor in a first period including a period prior to the occurrence of the learning-time event,
the processor is configured to derive ahe machine learning model using the learning-time event occurrence information and an information based on the first period information, as training data, in the second operation, and
the processor is configured to conduct the first operation, based on the machine learning model.

14. The data processor according to claim 13, wherein
the processor is configured to add a first annotation to the first period information, based on the learning-time event occurrence information, in the second operation, and
the training data includes the first period information to which the first annotation has been added.

15. The data processor according to claim 1, wherein
a part of the first data is obtained from a third sensor configured to detect the state of the human subject,
the first sensor includes a body movement sensor provided to a bed to be used by the human subject,
the third sensor includes an imaging device configured to image the human subject,
the second sensor includes at least one of an excretion device being used by the human subject, or an excretion sensor configured to detect excretion by the human subject,
the first event includes excretion, and
the state at the occurrence of the first event includes a prediction of at least one of a fall or a tumble.

16. The data processor according to claim 1, wherein
a part of the first data is obtained from a third sensor configured to detect the state of the human subject,
the first sensor includes a body movement sensor provided to a bed to be used by the human subject,
the third sensor includes an imaging device configured to image the human subject,
the second sensor includes a weighted sensor configured to detect weighting from the human subject,
the first event includes bed-leaving, and
the state at the occurrence of the first event includes a prediction of at least one of a fall or a tumble.

17. The data processor according to claim 15, wherein
the processor is configured to acquire a first information obtained from the first sensor, a second information obtained from the second sensor, and a third information obtained from the third sensor, in the second operation,
an amount of the first information is larger than an amount of the second information,
the second information includes a second event occurrence information related to an occurrence of a second event detected by the second sensor, and the second event corresponds to the first event,
the first information includes a first period information obtained from the first sensor in a first period including a period prior to the occurrence of the second event,
the third information includes second period information obtained from the third sensor in a second period including a period prior to the occurrence of the second event,
the processor is configured to derive the machine learning model using the second event occurrence information, an information based on the first period information, and an information based on the second period information, as training data, in the second operation, and
the processor is configured to conduct the first operation, based on the machine learning model.

18. The data processor according to claim 17, wherein
the processor is configured to add a first annotation to the first period information, and add a second annotation to the second period information, based on the second event occurrence information, in the second operation, and the training data includes the first period information to which the first annotation has been added, and the second period information to which the second annotation has been added.

19. A data processor comprising:
an acquisitor configured to acquire a first data corresponding to detected signals acquired from a first sensor and a second data acquired from a second sensor, the first sensor being different from the second sensor; and
a processor, in response to the first data being acquired by the acquisitor, configured to conduct a first operation and a second operation based on the first data and the second data acquired by the acquisitor,
at least a part of the first data being obtained from a first sensor configured to detect a state of a human subject,
the processor being configured to output and provide for display, in response to the first data including a first data information corresponding to signal intensity of the detected signals acquired first data exceeding a first threshold, an occurrence of a first event prediction information related to an occurrence of a first event related to the human subject and second event prediction information related to an occurrence of a second event after the first event, in the first operation, the first event being a physical activity of the human subject and the second event corresponds to the first event,
the occurrence of the first event being configured to be detected by the second sensor configured to detect the state of the human subject based on the second data, and
the occurrence of the second event being detected by a third sensor configured to detect the state of the human subject,
the processor being configured to add an annotation data to the second data, the annotation data being generated based on the first event prediction information and the physical state prediction information, and to generate a machine learning model for the second operation based on the second data and the annotation data, wherein the processor is configured to conduct the first operation based on the machine learning model.

20. The data processor according to claim 19, wherein the first event includes bed-leaving, and the second event includes excretion.

21. The data processor according to claim 19, wherein the first sensor includes a body movement sensor provided to a bed to be used by the human subject, the second sensor includes a weighted sensor configured to detect weighting from the human subject, and the third sensor includes at least one of an excretion device to be used by the human subject, or an excretion sensor configured to detect excretion by the human subject.

22. The data processor according to claim 1 wherein, the data processor is included in a care support system comprising:
the data processor;
the first sensor; and
a terminal device;
the terminal device including an output part, and
the output part being configured to output the first event prediction information and the state prediction information.

23. A data processing method comprising:
causing a processor to acquire a first data acquired from a first sensor and a second data acquired from a second sensor, the first sensor being different from the second sensor; and
in response to the first data being acquired causing the processor to conduct a first operation and a second operation based on the first data and the second data,
at least a part of the first data being obtained from a first sensor configured to detect a state of a human subject,
the processor being configured to output and provide for display, in response to the first data including a first data information corresponding to signal intensity of the detected signals acquired first data exceeding a first threshold, an occurrence of a first event prediction information related to an occurrence of a first event related to the human subject and a physical state prediction information related to a physical state to be predicted of the human subject at the occurrence of the first event, in the first operation, the first event being a physical activity of the human subject,
the occurrence of the first event being configured to be detected by the second sensor configured to detect the state of the human subject based on the second data, and
the physical state to be predicted of the human subject at the occurrence of the first event being configured not to be detected by the second sensor,
the processor being configured to add an annotation data to the second data, the annotation data being generated based on the first event prediction information and the physical state prediction information, and to generate a machine learning model for the second operation based on the second data and the annotation data, wherein the processor is configured to conduct the first operation based on the machine learning model.

* * * * *